United States Patent
Smith et al.

(10) Patent No.: US 11,844,519 B2
(45) Date of Patent: Dec. 19, 2023

(54) SYSTEMS, DEVICES, AND RELATED METHODS FOR FASTENING TISSUE

(71) Applicant: Boston Scientific Scimed, Inc., Maple Grove, MN (US)

(72) Inventors: Paul Smith, Smithfield, RI (US); Ramon Estevez, Lowell, MA (US); Kathryn Venuto, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/188,348

(22) Filed: Mar. 1, 2021

(65) Prior Publication Data
US 2021/0275168 A1    Sep. 9, 2021

Related U.S. Application Data

(60) Provisional application No. 62/984,542, filed on Mar. 3, 2020.

(51) Int. Cl.
*A61B 17/068* (2006.01)
*A61B 17/072* (2006.01)
*A61B 17/29* (2006.01)
*A61B 17/00* (2006.01)

(52) U.S. Cl.
CPC ........ *A61B 17/0686* (2013.01); *A61B 17/072* (2013.01); *A61B 17/07207* (2013.01); *A61B 2017/0034* (2013.01); *A61B 2017/07228* (2013.01); *A61B 2017/07257* (2013.01); *A61B 2017/07271* (2013.01); *A61B 2017/07278* (2013.01); *A61B 2017/07285* (2013.01); *A61B 2017/2937* (2013.01)

(58) Field of Classification Search
CPC .......... A61B 2017/07278; A61B 2017/07271; A61B 2017/07285; A61B 17/07207
See application file for complete search history.

(56) References Cited

U.S. PATENT DOCUMENTS 5,452,836 A * 9/1995 Huitema .............. A61B 17/072
                                                 227/176.1
5,478,003 A * 12/1995 Green .............. A61B 17/07207
                                                 227/176.1
5,489,058 A * 2/1996 Plyley .............. A61B 17/07207
                                                 227/176.1

(Continued)

FOREIGN PATENT DOCUMENTS

EP    3366228 A2    8/2018

*Primary Examiner* — Gloria R Weeks
*Assistant Examiner* — Mobeen Ahmed
(74) *Attorney, Agent, or Firm* — Bookoff McAndrews, PLLC

(57) ABSTRACT

According to one aspect, a tissue fastening device may comprise a body configured to include a plurality of fasteners; an anvil rotatable relative to the body; and a tissue cutting device. The body may define a longitudinal channel configured to receive the tissue cutting device. The tissue fastening device may further comprise a fastener actuator configured to move proximally relative to the body to deploy the plurality of fasteners from the body; and an actuation wire coupled to the tissue cutting device and the fastener actuator. The actuation of the actuation wire may cause the fastener actuator to deploy at least one of the plurality of fasteners into tissue distally of tissue cut by the tissue cutting device.

16 Claims, 6 Drawing Sheets

(56) References Cited

U.S. PATENT DOCUMENTS

| | | | | |
|---|---|---|---|---|
| 5,632,432 A * | 5/1997 | Schulze | A61B 17/07207 | 227/176.1 |
| 5,816,471 A * | 10/1998 | Plyley | A61B 17/07207 | 227/19 |
| 6,010,054 A * | 1/2000 | Johnson | A61B 17/07207 | 227/176.1 |
| 7,695,485 B2 * | 4/2010 | Whitman | A61B 17/3201 | 606/142 |
| 8,167,898 B1 * | 5/2012 | Schaller | A61B 17/3209 | 227/180.1 |
| 8,365,975 B1 * | 2/2013 | Manoux | A61B 17/07207 | 227/176.1 |
| 9,084,600 B1 * | 7/2015 | Knodel | A61B 17/07207 | |
| 9,597,074 B2 * | 3/2017 | Felder | A61B 17/072 | |
| 9,700,320 B2 * | 7/2017 | Dinardo | A61B 17/07207 | |
| 9,737,299 B2 * | 8/2017 | Yan | A61B 17/07207 | |
| 10,765,425 B2 * | 9/2020 | Yates | A61B 17/068 | |
| 2001/0030219 A1 * | 10/2001 | Green | A61B 17/07207 | 227/175.1 |
| 2004/0199181 A1 * | 10/2004 | Knodel | A61B 17/07207 | 606/139 |
| 2005/0006432 A1 * | 1/2005 | Racenet | A61B 17/105 | 227/176.1 |
| 2007/0034667 A1 * | 2/2007 | Holsten | A61B 17/072 | 227/176.1 |
| 2007/0175950 A1 * | 8/2007 | Shelton | A61B 17/07207 | 227/176.1 |
| 2007/0175952 A1 * | 8/2007 | Shelton | A61B 17/07207 | 227/176.1 |
| 2007/0194079 A1 * | 8/2007 | Hueil | B25C 5/0292 | 227/176.1 |
| 2008/0149684 A1 * | 6/2008 | Viola | A61B 17/07207 | 227/176.1 |
| 2008/0308607 A1 * | 12/2008 | Timm | A61B 17/07207 | 227/176.1 |
| 2009/0065552 A1 * | 3/2009 | Knodel | A61B 17/1222 | 227/180.1 |
| 2010/0252611 A1 | 10/2010 | Ezzat et al. | | |
| 2011/0204120 A1 * | 8/2011 | Crainich | A61B 17/07207 | 227/180.1 |
| 2011/0248064 A1 * | 10/2011 | Marczyk | A61B 17/07207 | 227/114 |
| 2012/0074202 A1 * | 3/2012 | Knodel | A61B 17/072 | 227/180.1 |
| 2013/0008937 A1 * | 1/2013 | Viola | A61B 17/0686 | 227/177.1 |
| 2013/0056522 A1 * | 3/2013 | Swensgard | A61B 17/07292 | 227/176.1 |
| 2013/0105545 A1 * | 5/2013 | Burbank | A61B 17/07207 | 227/175.1 |
| 2013/0153636 A1 * | 6/2013 | Shelton, IV | A61B 17/0643 | 227/176.1 |
| 2013/0175316 A1 * | 7/2013 | Thompson | A61B 17/1222 | 227/175.1 |
| 2013/0181035 A1 * | 7/2013 | Milliman | A61B 17/1155 | 227/180.1 |
| 2014/0025105 A1 * | 1/2014 | Whitman | A61B 17/07207 | 606/219 |
| 2014/0263567 A1 * | 9/2014 | Williams | A61B 17/07207 | 227/180.1 |
| 2015/0105823 A1 * | 4/2015 | Racenet | A61B 34/71 | 227/176.1 |
| 2015/0173756 A1 * | 6/2015 | Baxter, III | A61B 17/0644 | 227/177.1 |
| 2015/0297236 A1 * | 10/2015 | Harris | A61B 17/1222 | 227/176.1 |
| 2016/0166256 A1 * | 6/2016 | Baxter, III | A61B 17/07207 | 227/176.1 |
| 2016/0192917 A1 * | 7/2016 | Shelton, IV | A61B 17/2812 | 606/1 |
| 2017/0056015 A1 * | 3/2017 | Harris | A61B 17/07207 | |
| 2017/0112561 A1 | 4/2017 | Motai | | |
| 2017/0128121 A1 * | 5/2017 | Takashino | A61B 18/10 | |
| 2019/0046193 A1 * | 2/2019 | Dunki-Jacobs | A61B 17/072 | |
| 2019/0125342 A1 * | 5/2019 | Beardsley | A61B 17/072 | |
| 2019/0282233 A1 * | 9/2019 | Burbank | A61B 17/07207 | |
| 2020/0113561 A1 * | 4/2020 | Schings | A61B 17/115 | |
| 2021/0038223 A1 * | 2/2021 | Schings | A61B 17/07207 | |
| 2021/0282777 A1 * | 9/2021 | Thompson | A61B 17/07207 | |

\* cited by examiner

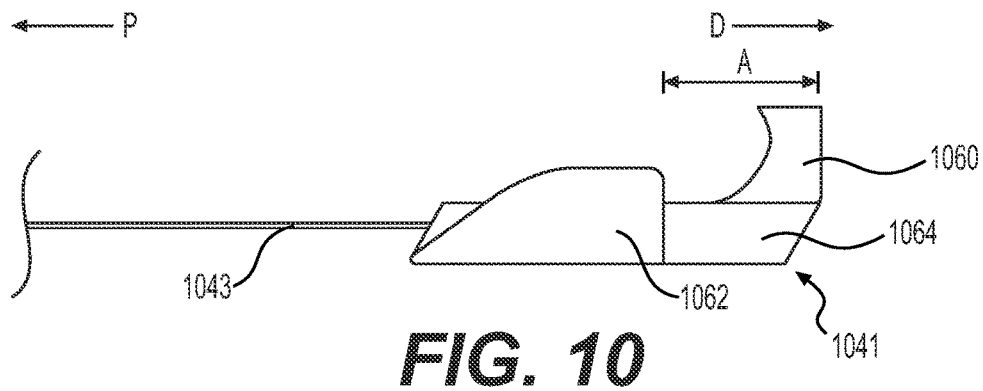
FIG. 10
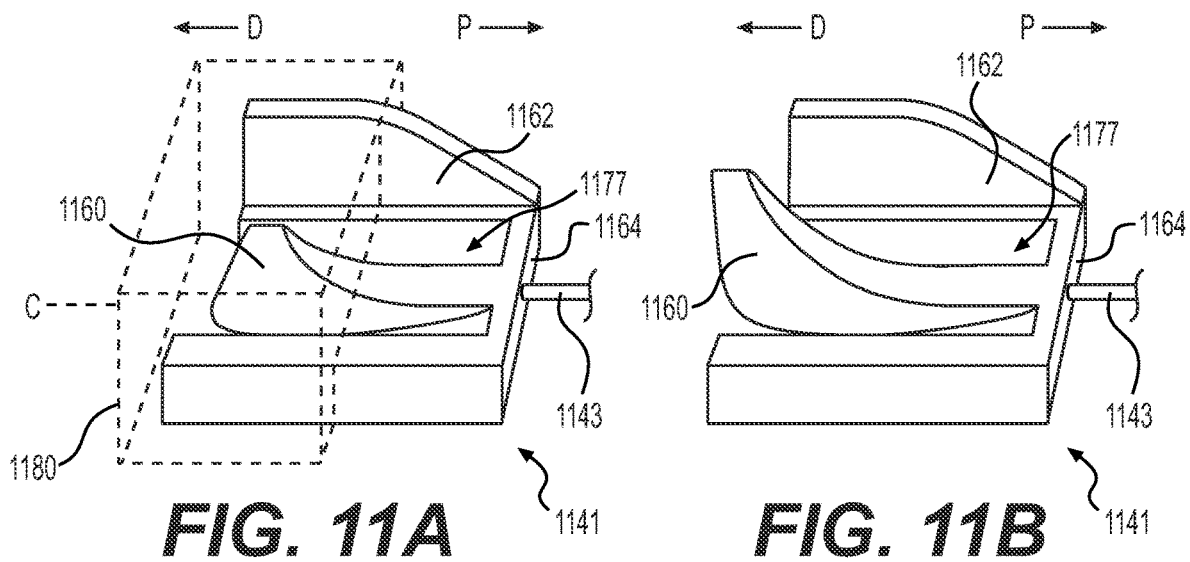
FIG. 11A            FIG. 11B
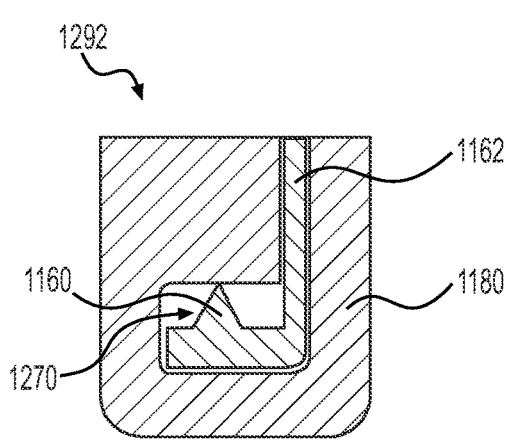            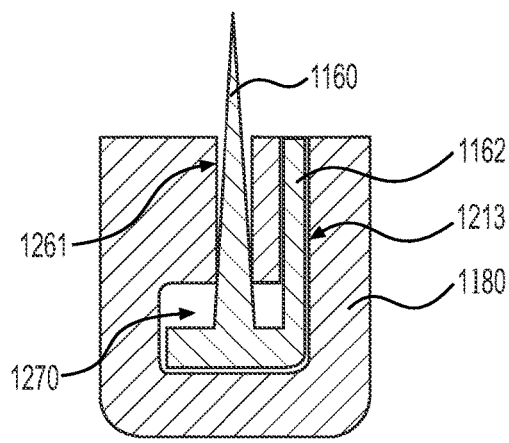
FIG. 12A            FIG. 12B

SYSTEMS, DEVICES, AND RELATED METHODS FOR FASTENING TISSUE

CROSS-REFERENCE TO RELATED APPLICATIONS

This application claims the benefit of priority from U.S. Provisional Application No. 62/984,542, filed on Mar. 3, 2020, which is incorporated by reference herein in its entirety.

TECHNICAL FIELD

Various aspects of this disclosure relate generally to tissue fastening and resecting, including visualizing, retracting, coupling, and/or cutting tissue. For example, embodiments of the disclosure relate to systems, devices, and related methods for stapling and separating tissue, among other aspects.

BACKGROUND

Technological developments have given users of medical systems, devices, and methods, the ability to conduct increasingly complex procedures on subjects. The coupling of tissue in, for example, a subject's gastrointestinal tract, is a type of procedure in which difficulties may arise. Surgical devices that grasp or clamp tissue between opposing jaw structures and then join the tissue by surgical fasteners are known. The fasteners include surgical staples. In some procedures, a cutting instrument is provided to cut the tissue which has been joined by the fasteners. However, problems may arise when stapling and cutting tissue in order to remove tumorous tissue from a patient's body.

SUMMARY

Aspects of the disclosure relate to, among other things, systems, devices, and methods for fastening tissue and/or cutting tissue. Each of the aspects disclosed herein may include one or more of the features described in connection with any of the other disclosed aspects.

According to one aspect, a tissue fastening device may comprise a body configured to include a plurality of fasteners; an anvil rotatable relative to the body; and a tissue cutting device. The body may define a longitudinal channel configured to receive the tissue cutting device. The tissue fastening device may further comprise a fastener actuator configured to move proximally relative to the body to deploy the plurality of fasteners from the body; and an actuation wire coupled to the tissue cutting device and the fastener actuator. The actuation of the actuation wire may cause the fastener actuator to deploy at least one of the plurality of fasteners into tissue distally of tissue cut by the tissue cutting device.

In other aspects, the device may include one or more of the features below. The tissue fastening device may be configured to deploy fasteners distal to the longitudinal channel. The tissue cutting device and the fastener actuator may be a U-shaped component; and legs of the U-shaped component may be substantially parallel and comprise the tissue cutting device and the fastener actuator. The tissue cutting device may be distal to the fastener actuator. The tissue cutting device and the fastener actuator may be unitary. The body may include a ramp portion configured to transition the tissue cutting device from 1) an undeployed state in which the tissue cutting device is within the body and incapable of cutting tissue, and 2) a deployed state in which the tissue cutting device is exposed outside of the body and capable of cutting tissue. The device may further comprise a first spacer and a second spacer, and each of the first spacer and the second spacer may be within the body and configured to deploy a fastener, and the first spacer may have a different height than the second spacer.

In other aspects, the device may include one or more of the features below. Activation of the actuation wire may cause the fastener actuator to deploy the at least one of the plurality of fasteners before causing the tissue cutting device to cut tissue. The tissue cutting device may be biased towards a relaxed position in alignment with the longitudinal channel; and the tissue cutting device may be configured to transition from a stressed position within the body to the relaxed position partially outside the body when the tissue cutting device moves proximally. The fastener actuator may be coupled to the actuation wire via a first connecting wire, the tissue cutting device may be coupled to the actuation wire via a second connecting wire, and the tissue cutting device may be distal to the fastener actuator. The fastener actuator may be directly coupled to the actuation wire, and the tissue cutting device may be movably coupled to the actuation wire via a coupler. The tissue cutting device may be coupled to the actuation wire via a connecting wire, and the connecting wire may include a spring portion. The spring portion may include a spring-loaded coil within a housing. The fastener actuator may be directly coupled to the actuation wire, the actuation wire may include a spring portion, the tissue cutting device may be movably coupled to a portion of the actuation wire proximal to the spring portion, and the tissue cutting device may be coupled to the actuation wire via a coupler. The body may include a U-shaped channel configured to receive the tissue cutting device and the fastener actuator, and the U-shaped channel may be connected to the longitudinal channel.

In another aspect, a tissue fastening device may comprise a body configured to include a plurality of fasteners; an anvil rotatable relative to the body; and a tissue cutting device. The body may define a longitudinal channel configured to receive the tissue cutting device. The tissue fastening device may further comprise a fastener actuator configured to move proximally relative to the body to deploy the plurality of fasteners from the body; and an actuation wire coupled to the tissue cutting device and the fastener actuator. The actuation of the actuation wire may cause the fastener actuator to deploy at least one of the plurality of fasteners into tissue prior to causing the tissue cutting device to cut tissue.

In other aspects, the device may include one or more of the features below. The longitudinal channel may be configured so that it receives the tissue cutting device in a position to cut tissue, distally of a distalmost fastener of the plurality of fasteners. The plurality of fasteners may define a line of fasteners, and a distalmost part of the line is distal to a cut line defined by the longitudinal channel.

In another aspect, a method of fastening tissue may include advancing a fastening device including an anvil and a body to a target site within a patient. The fastening device may include an open configuration and a closed configuration, and a distance between distal end of the anvil and the distal end of the body may be greater in the open configuration than a distance between the distal end of the anvil and the distal end of the body in the closed configuration. The method may further include moving the anvil and the body from the open configuration to the closed configuration; and pulling an actuation wire proximally to move a fastener actuator and a tissue cutting device simultaneously in the proximal direction within the body, causing the fastener actuator to deploy at least one fastener into tissue distal of a cut of tissue by the tissue cutting device.

In some examples, the method may also include transitioning the tissue cutting device from 1) a first state in which the tissue cutting device is positioned within the body and incapable of cutting tissue, to 2) a second state in which the tissue cutting device is exposed outside of the body and capable of cutting tissue.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of this disclosure and together with the description, serve to explain the principles of the disclosure.

FIG. 10 is a perspective view of a portion of an exemplary medical device, according to aspects of this disclosure.

FIGS. 11A and 11B are configurations of a portion of an exemplary medical device, according to aspects of this disclosure.

FIGS. 12A and 12B are front cross-sectional views of portions of an exemplary medical device, according to aspects of the present disclosure.

DETAILED DESCRIPTION

Figure 1:
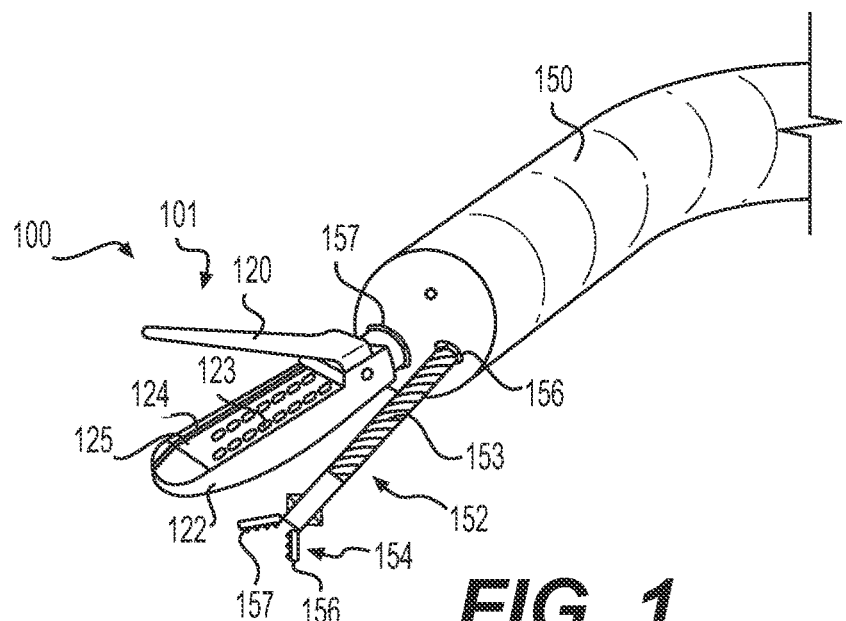
FIG. 1 is a perspective view of an exemplary surgical system, according to aspects of this disclosure.

This disclosure is drawn to systems, devices, and methods for coupling, cutting, and/or resecting tissue, among other aspects. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. The term "coupling tissue together" may refer, for example, to stapling, fixing, attaching, fastening, or otherwise joining two portions of tissue together. The term "fastener" may include staples, clips, elastic bands, suture, or any other fastener known in the art. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately" indicate a range of values within +/−10% of a stated value.

Embodiments of this disclosure may address difficulties in stapling tissue together during a procedure. One such difficulty involves removing a lesion from tissue. In order to remove a lesion, the user may staple tissue around the outer edge of the lesion. When a lesion is highly contagious, it is important to cut the tissue at a region that does not include the lesion to avoid spreading the contagious tissue.

Often surgical staplers include a staple cartridge to house a plurality of staples. An anvil defines a surface for forming the staple legs as the staples are driven from the staple cartridge. The stapling operation may be effected by an actuator acting upon a staple, which may involve pushing the actuator in a distal direction to drive the staples from the cartridge. With such a configuration, problems may arise when pushing the actuator due to curves in portions of the stapler connecting its proximal and distal ends, and a user may find it difficult to actuate the stapler when the stapler is rotated or angled from a longitudinally straight position. Embodiments of this disclosure may address these or other issues related to surgical staplers and related devices.

Embodiments of this disclosure may be used to visualize, cut, resect, and/or couple together target tissue in an endoluminal space, or facilitate the process thereof. For example, some embodiments combine a tissue resecting device with a tissue stapling device. A tissue stapling apparatus may include a resection or cutting mechanism (e.g., an integrated knife) and a stapling mechanism (stapler). The stapling apparatus may be delivered to target tissue through an endoscope working channel to the target tissue site. The overall system may include a retraction mechanism, such as a tissue clip or grasper, to pull tissue towards the tissue stapling device. All or parts of the tissue stapling device and the retraction mechanism could be metallic, plastic, a shape memory metal (such as nitinol), a shape memory polymer, a polymer, or any combination of materials.

FIG. 1 shows a distal section of an endoscope 150, a tissue acquisition tool 152 positioned within a working channel 156 of the endoscope 150, and a surgical apparatus 100 positioned within another working channel 157 of the endoscope 150, in accordance with an embodiment of this disclosure. Endoscope 150 may include an imaging assembly, such as a camera, at its distal end to visualize surgical apparatus 100 at a target region of a patient's body. Surgical apparatus 100 is a surgical stapling apparatus or stapler device configured to engage body tissue, apply a plurality of surgical fasteners thereto, and form an incision in the fastened body tissue during minimally invasive surgical procedures, such as laparoscopic or endoscopic procedures. Apparatus 100 may be used to apply surgical clips or other fasteners, but will be primarily discussed in the context of applying staples from a staple cartridge, such as a loading unit, positioned in a portion of the device's body.

As illustrated in FIG. 1, surgical apparatus 100 may include a stapler device 101, a body portion (not shown) extending through working channel 157, and a proximal portion (not shown) including one or more actuators. In some examples, stapler device 101 may be pushed in a distal direction through working channel 157 to position stapler device 101 at a distal end of surgical apparatus 100, and in other examples, stapler device 101 may be back-fed through working channel such that the proximal portion of stapler device 101 is moved through working channel 157 to position stapler device 101 at a distal end of surgical apparatus 100. The body portion may include a lumen for positioning actuation wires within, and actuation wires may be configured for actuating the stapler device 101 via one or more actuators (not shown) or actuating any other portion of apparatus 100. In some examples, surgical apparatus 100 may include a handle assembly (not shown) including one or more actuators at a proximal portion of the apparatus. A detailed description of various embodiments of surgical apparatus 100 and its operation is described in U.S. Non-provisional patent application Ser. No. 16/804,887, filed Feb. 28, 2020, which is incorporated herein by reference in its entirety.

Stapler device 101 may include an anvil 120 and a cartridge 122. In some examples, cartridge 122 may be integrally formed in stapler device 101 (shown in FIG. 1). An anvil 120 may be rotatably or pivotably coupled to cartridge 122, and may extend distally towards a distal end of stapler device 101. In some examples, anvil 120 may be rotatably biased and may be biased to an open configuration, e.g. biased away from cartridge 122 creating a space between the distal portion of anvil 120 and the distal portion of cartridge 122. Anvil 120 may be rotatable to pinch tissue between anvil 120 and cartridge 122, and provide a surface for which staples may be driven when ejected from cartridge 122.

Figure 3:
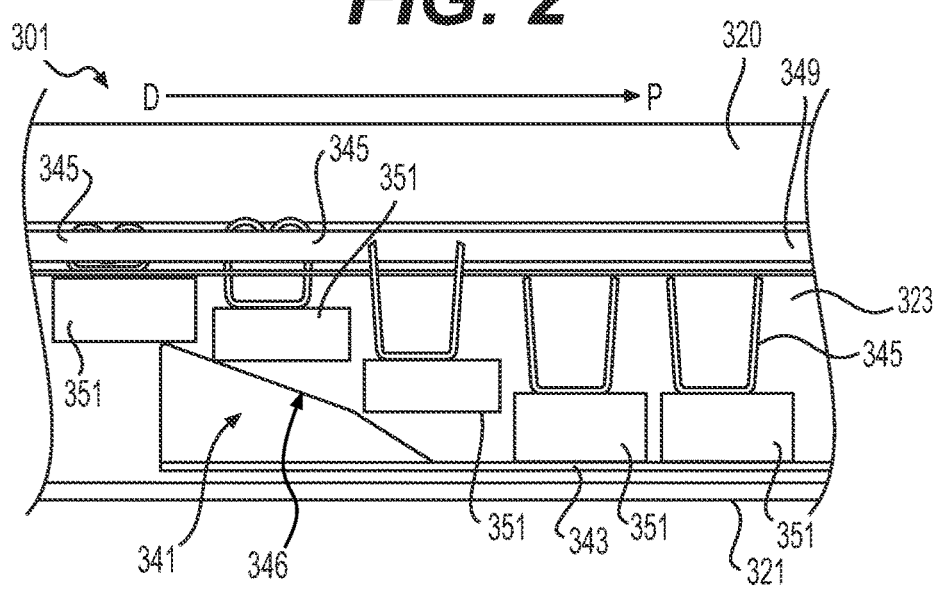
FIG. 3 is a cross-sectional view of a portion of an exemplary medical device, according to aspects of the present disclosure.

Cartridge 122 may contain a plurality of surgical fasteners, such as staples, and the fasteners may be deployed from cartridge 122 when under the influence of a driving force exerted by an actuation sled, such as actuation sled 341 shown in FIG. 3. A plurality of spaced apart longitudinal slots 123 in cartridge 122 allow staples to pass through cartridge 122 and pierce tissue. In some examples, actuation sled 341 moves proximally in the longitudinal direction from a distal end of cartridge 122 when actuated, contacting fasteners (directly or indirectly) within cartridge 122, and pushing fasteners through longitudinal slots 123 in order to couple fasteners to tissue. In some examples, a single fastener may extend through each slot 123. Each fastener may be partially within a slot 123 prior to deployment to assist with alignment of the fastener with the slot 123. In some examples, two actuation sleds 341 may be used to actuate two different longitudinal rows of fasteners in cartridge 122. In other examples, a single actuation sled 341 may be used to actuate two different longitudinal rows of fasteners, such as with assistance of spacers 351 (shown in FIG. 3) within cartridge 122.

Cartridge 122 may also include an elongate longitudinal slot 124. The elongate longitudinal slot 124 may be configured to receive and/or support a resecting tool, such as a knife blade (for example knife 242 shown in FIG. 2). The elongate longitudinal slot 124 may be positioned on a side of cartridge 122 and may run longitudinally from the proximal end to the distal end of cartridge 122. In some examples, each of the spaced apart longitudinal slots 123 may be positioned on one side of the elongate longitudinal slot 124. Anvil 120 may include a groove (not shown) positioned longitudinally that may align with elongated longitudinal slot 124 when anvil 120 is in the closed position (e.g. anvil 120 is rotated such that a distal portion of anvil 120 comes into contact with cartridge 122, or pinches tissue between anvil 120 and cartridge 122) and such groove may be configured to receive a resecting tool such as a knife or other sharp cutting tool within the elongate longitudinal slot 124. The cutting tool may be actuated via an additional, separate actuation wire from the actuation wire that translates the actuation sled (such as actuation sled 241 or 341), or may be actuated via the same actuation wire as the actuation sled to translate both the actuation sled and the cutting tool at the same time. For example, the stapling mechanism and the cutting mechanism may be integral such that actuation of the actuation sled similarly actuates a tissue separation tool.

Figure 2:
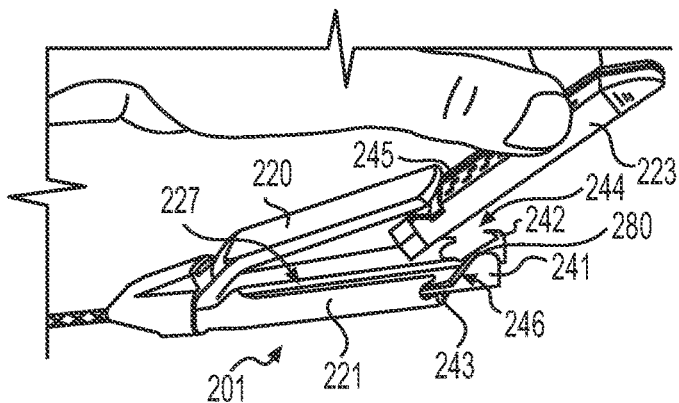
FIG. 2 is a perspective view of an exemplary medical device, according to aspects of this disclosure, including a component being inserted into the device by a user.

FIG. 2 shows a distal portion of an embodiment of stapler device 201 that is configured to receive a removable cartridge 223. When cartridge 223 is removed from body 221, actuation sled 241 and knife 242 may be visible (as shown in FIG. 2). In some examples, when cartridge 223 is positioned within a channel 227 of body 221, actuation sled 241 and knife 242 may be received within cartridge 223 and may not be visible. In other examples, actuation sled 241 and knife 242 may be received within cartridge 223 and may be visible when cartridge 223 is positioned within body 221, such as by extending out of channels in cartridge 223. Actuation sled 241 and knife 242 may be coupled to a single actuation wire extending to a proximal portion of stapler device 201 such that, when actuated, actuation sled 241 and knife 242 move proximally in unison. Actuation sled 241 may be configured to be translated proximally to push fasteners, such as staples within cartridge 223, out of slots 245 in cartridge to fasten tissue together. Actuation sled 241 and knife 242 may be pressed by the user into a distal pocket of cartridge 223 when cartridge 223 is first positioned within body 221.

Actuation sled 241 may include a ramp 246 that is configured to engage, directly or indirectly, staples, or other fasteners from within cartridge 223 through slots 245, to deploy fasteners to couple tissue. In some examples, ramp 246 may be angled at 45 degrees, 40 degrees, 35 degrees, 30 degrees, 25 degrees, or any other angle relative to a longitudinal axis of body 221. Ramp 241 may be a shallow angle to require the actuation sled 241 to translate proximally for a longer distance in order to deploy fasteners in cartridge 223. By providing actuation sled 241 with a shallow angle, long ramp 241, a user may engage multiple fasteners at the same time when pulling actuation sled 241 proximally. By engaging multiple fasteners at the same time, in some examples, multiple staples may deploy and pierce tissue at the same time. Furthermore, a shallow angle ramp 246, e.g. an angle approximately 30 degrees or less, may prevent intermittent forces being applied to the actuator in the handle assembly due to the actuation sled 241 releasing from a fastener before engaging the next fastener. By continuously engaging fasteners in cartridge 223, ramp 246 may prevent errors during a procedure by providing a more continuous force applied to the actuator. In some examples, ramp 246 of actuation sled 241 may engage two, three, four, or more fasteners in cartridge 223 at the same time. Since actuation sled 241 is pulled proximally to deploy fasteners, a user may generate higher loads compared to a pushing mechanism to deploy fasteners. An actuation body 243 may extend proximally from a proximal portion of ramp 246, and actuation sled 241 may be pulled by the actuation body 243 to deploy fasteners. For example, actuation body 243 may be coupled to an actuation wire that extends to a proximal portion of stapler device 201. In some examples, stapler device 201 may include two actuation sleds 241 and two actuation bodies 243 coupled to the same actuation wire to engage and deploy two separate rows of fasteners in cartridge 223.

Knife 242 may have a similar structure to actuation sled 241 and may include a hooked distal portion 244 that includes sharp edges for cutting tissue. Knife 242 may be configured to travel longitudinally within an elongated longitudinal slot 245 of cartridge 223. In some examples, a portion of knife 242 extends into a groove of anvil 220 and travels within the groove longitudinally from the distal end of anvil 220 to the proximal end when a user actuates knife 242, thus translating knife 242 longitudinally across cartridge 223 to cut tissue.

A user may use stapler device 201 to couple one or more fasteners to tissue by first positioning tissue within the active region of stapler device 201, e.g. between body 221 and anvil 220. Once tissue is positioned in the active region of stapler device 201, a user may actuate an actuator at a proximal portion of stapler device 201, which may then translate an actuation wire proximally and cause anvil 220 to close onto the tissue positioned within the stapler device's active region. While the user holds anvil 220 in an engaged position, thus maintaining the stapler device's clasp on the tissue, the user may translate an actuation wire coupled to actuation body 243 proximally. When the actuation sled 241 is translated proximally via actuation body 243 coupled to the actuation wire, ramp 246 of actuation sled 241 may engage a fastener in cartridge 223 and push the fastener through a longitudinal slot (such as 123 in FIG. 1) to pierce the tissue. When the fastener is deployed by actuation sled 241, the fastener may subsequently engage anvil 220 (e.g. to form a final staple configuration) and couple layers of tissue together. In some examples, the user may actuate an actuation wire coupled to both actuation sled 241 and knife 242, and may translate both actuation sled 241 and knife 242 simultaneously to both pierce and fasten tissue with one or more fasteners and cut tissue.

A user may use a tissue acquisition tool 152 in combination with a stapler device 101 to facilitate grabbing tissue and positioning tissue in the active portion of stapler device 101, e.g. between cartridge 122 and anvil 120, for stapling. Tissue acquisition tool 152 may include an elongate body 153 extending longitudinally to a distal end portion 154. In some examples, distal end portion 154 of tissue acquisition tool 152 may include a pair of rotatable jaws 156, 157 that are moveable between a closed configuration and an open configuration. A user may actuate jaws 156, 157 using an actuator present at the proximal portion of tissue acquisition tool 152 (not shown) to open and close jaws 156, 157 to facilitate grabbing and releasing tissue. A user may position tissue acquisition tool 152 within a working channel 156, as shown in FIG. 1, separate from the working channel 157 in which the stapler device 101 is positioned. In other examples, a user may position tissue acquisition tool 152 in the same working channel as stapler device 101 (not shown) to facilitate positioning tissue between anvil 120 and cartridge 122.

FIG. 3 shows an enlarged, cross-sectional view of an exemplary stapler device 301 including body 321, anvil 320, cartridge 323 with fasteners 345, and actuation sled 341 with actuation body 343. The stapler device 301 in FIG. 3 is shown deploying fasteners 345 into tissue 349. Actuation sled 341 engages pistons or spacers 351, and the pistons or spacers 351 then engage the fasteners 345 to deploy the fasteners 345. Actuation sled 341 engages the pistons or spacers 351 as actuation sled 341 moves in the proximal direction P. Each piston or spacer 351 may be configured to translate within cartridge 323 and may be sized to engage only one fastener. In other examples, each piston or spacer 351 may be sized to engage multiple fasteners, or one or more pistons or spacers 351 may be sized to engage multiple fasteners while one or more other pistons or spacers 351 may be sized to engage only one fastener. In some examples, each spacer 351 may be positioned within a slot within cartridge 323 restricting the proximal-distal movement of the spacer 351 while allowing movement transverse to the proximal-distal direction. Actuation sled 341 may be configured to move each piston or spacer 351 in a direction transverse to the longitudinal axis of body 321. For example, actuation sled 341 and actuation body 343 may be pulled proximally via an actuation wire, which may move ramp 346 into contact with one or more pistons or spacers 351 and push one or more pistons or spacers 351 to deploy one or more fasteners 345 from cartridge 323.

Each of the pistons or spacers 351 may have an upper surface that aligns and/or is flush with a portion of each respective fastener 345. For example, each fastener 345 may be a staple and may include three substantially flat sections with the middle substantially flat section aligning with the top surface of each spacer 351. Each piston or spacer 351 may be sufficiently rigid to move uniformly upward when the ramp 346 of actuation sled engages a corner of the piston or spacer 351. In some examples, each piston or spacer 351 may be coupled to cartridge 323 such that movement along the longitudinal axis of cartridge 323, or in the proximal P or distal D directions shown in FIG. 3, is prevented while allowing movement in a direction perpendicular to the longitudinal axis of cartridge 323. The pistons or spacers 351 in cartridge 323 may prevent fasteners 345, such as staples, from partially deploying and may avoid improper stapling caused by a distal portion of a staple moving upward when a proximal portion of the staple does not move. By providing spacers 351 with flat top surfaces that align with fasteners 345, the ramp 342 of actuation sled 341 can move proximally and push each fastener 345 uniformly upward by engaging each spacer.

When actuation sled 341 is actuated, for example pulled from its proximal end proximally via an actuation mechanism, ramp 346 will engage fastener 345 (directly or indirectly through spacer 351) and translate fastener towards tissue 349 to pierce tissue 349, as the actuation sled 341 moves in the proximal direction. When fastener 345 is translated through tissue 349 via engagement with actuation sled 341, portions of fastener 345 may be pushed towards each other via engagement with anvil 320 and may cause fastener to clasp onto tissue 349.

Figure 4:
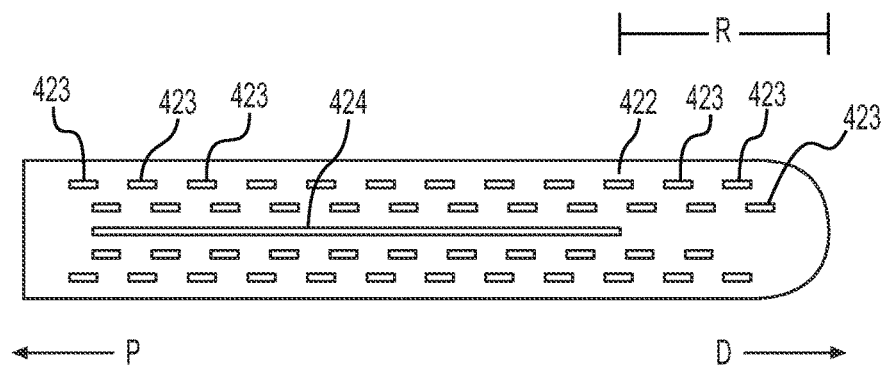
FIG. 4 is a top view of an exemplary stapler cartridge, according to aspects of the present disclosure.

FIG. 4 shows a top view of an exemplary stapler cartridge 422 including a plurality of longitudinal slots 423 configured to receive fasteners and an elongate longitudinal slot 424 configured to receive and/or support a resecting tool, such as knife 242. Some of the plurality of longitudinal slots 423 are positioned distal to elongate longitudinal slot 424 within region R (shown in FIG. 4), which provides a line of fasteners that extend beyond the cut line (or a line created by knife 242 when deployed from elongate longitudinal slot 424), which may prevent leakage of bodily fluid when stapling two portions of tissue together. For example, region R may extend approximately 8 mm (or any other suitable distance) distal from the distal end of elongate longitudinal slot 424. Cartridge 422 includes two rows of slots 423 on each side of elongate longitudinal slot 424, and the slots of one row of slots 423 are staggered longitudinally from the slots 423 of the adjacent row.

Figure 5:
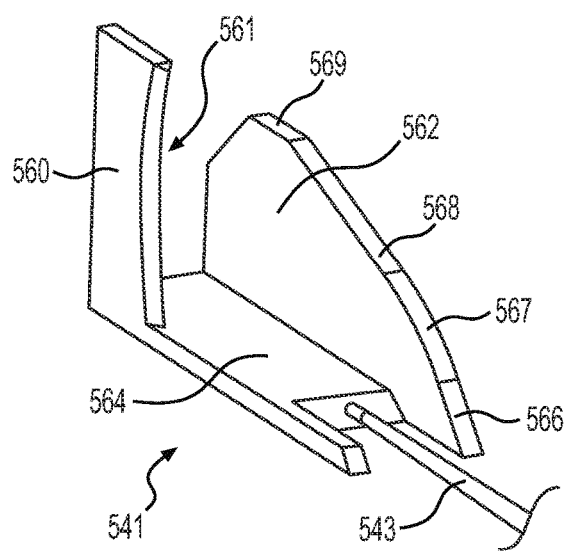
FIG. 5 is a perspective view of a portion of an exemplary medical device, according to aspects of this disclosure.

FIG. 5 shows a perspective view of an exemplary actuation sled 541 including a ramp portion 562 and a knife portion 560. A base portion 564, at a bottom of sled 541, may connect ramp portion 562 to knife portion 560, and an actuation wire 543 may extend proximally from base portion 564 to a proximal end of the stapler device in which actuation sled 541 is positioned within. Ramp portion 562 may include a plurality of ramps 566, 567, 568, 569 with varying inclines. By changing the incline at different portions of ramp portion 562, the amount of force applied to deploy fasteners from the cartridge is adjusted. For example, ramps 566, 567 may have a high incline to provide an initial large force applied to fasteners within a cartridge as actuation sled 541 is pulled proximally, and ramps 568, 569 may have a lower incline relative to ramps 566, 567 to decrease the amount of force applied to fasteners within the cartridge as actuation sled 541 moves proximally. Knife portion 560 may include a sharp edge 561 configured to cut or separate tissue. In some examples, ramp 562, base 564, and knife 560 may be unitary, and in other examples may be separate components fixedly coupled together.

Figure 6:
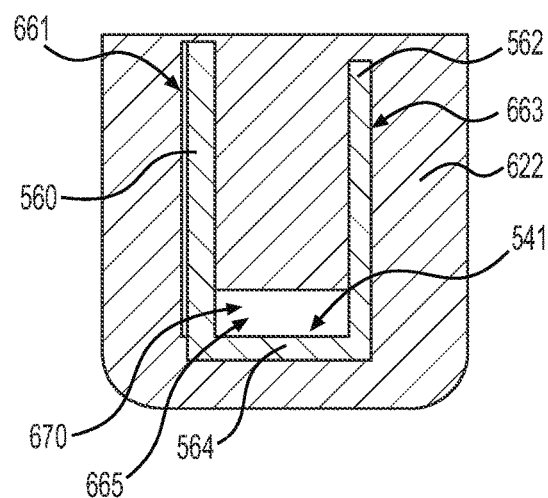
FIG. 6 is a front cross-sectional view of a portion of an exemplary medical device, according to aspects of this disclosure.

FIG. 6 shows a cross-sectional view of actuation sled 541 positioned within a cartridge 622 including a U-shaped channel 670 configured to receive actuation sled 541. The cross-sectional view of FIG. 6 is shown at axis Z in FIG. 7 along the length of cartridge 622, with actuation sled 541 positioned at a distal end of cartridge 622. A stapling portion 663 of channel 670 may be in communication with longitudinal slots (such as longitudinal slots 423) of cartridge 622, and resecting portion 661 of channel 670 may be in communication with an elongate longitudinal slot (such as slot 424) of cartridge 622. A connecting portion 665 of channel 670 may connect stapling portion 663 to resecting portion 661. Channel 670 may be configured to allow actuation sled 541 to translate through channel 670 in the proximal and distal directions through cartridge 622. Actuation sled 541 may provide a means to both deploy fasteners 345 and cut tissue via actuation of a single actuation wire 543.

Figure 7:
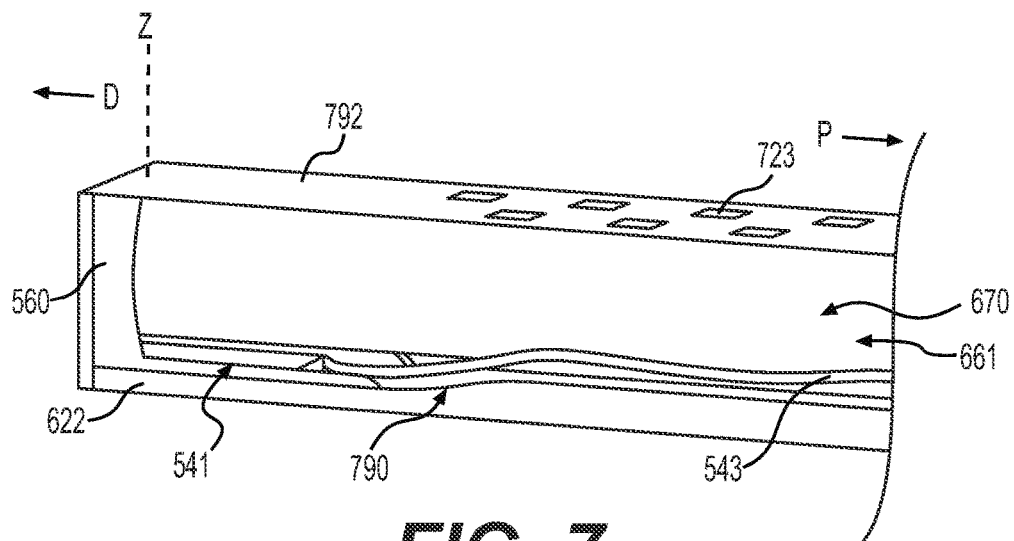
FIG. 7 is a side view of a portion of an exemplary medical device, according to aspects of this disclosure.
Figure 8:
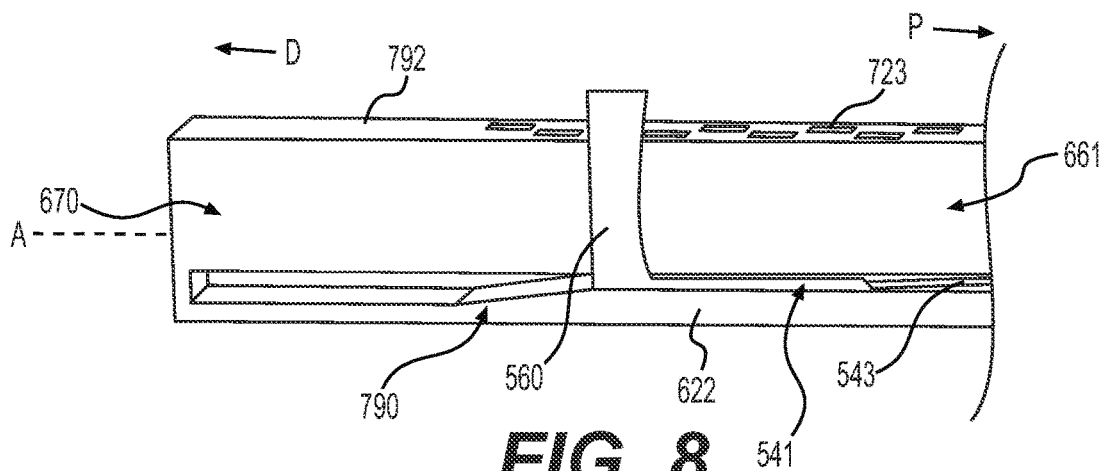
FIG. 8 is a side view of a portion of an exemplary medical device, according to aspects of this disclosure.

FIGS. 7 and 8 show side views of cartridge 622 with a portion of cartridge 622 removed to show resection portion 661 of channel 670. Actuation wire 543 is shown extending through connecting portion 665, and knife 560 is positioned within resection portion 661 of channel 670. Connecting portion 665 may include a ramp portion 790 that includes a curved and/or slanted surface extending in the proximal-distal direction. Ramp portion 790 may include a surface extending towards a central longitudinal axis A as the ramp portion extends proximally. Ramp portion 790 may be configured to transition knife portion 560 from an undeployed position within cartridge 622 (shown in FIG. 7) to a deployed position with a portion of knife portion 560 extending outward from cartridge 622 (shown in FIG. 8), exposing a portion of knife portion 560 outside of cartridge 622 as actuation sled 541 is pulled proximally. Ramp 790 may be slanted such that actuation sled 541 moves upward towards top surface 792 of cartridge 622 when actuation sled 541 is pulled proximally and moves across ramp 790. Ramp 790 may extend gradually away from a central longitudinal axis A of cartridge 622 as ramp 790 extends in a distal direction. A surface defining connecting portion 665 that is distal of ramp portion 790 is further from top surface 792 than is a surface of connecting portion 665 proximal of ramp portion 790.

Figure 9:
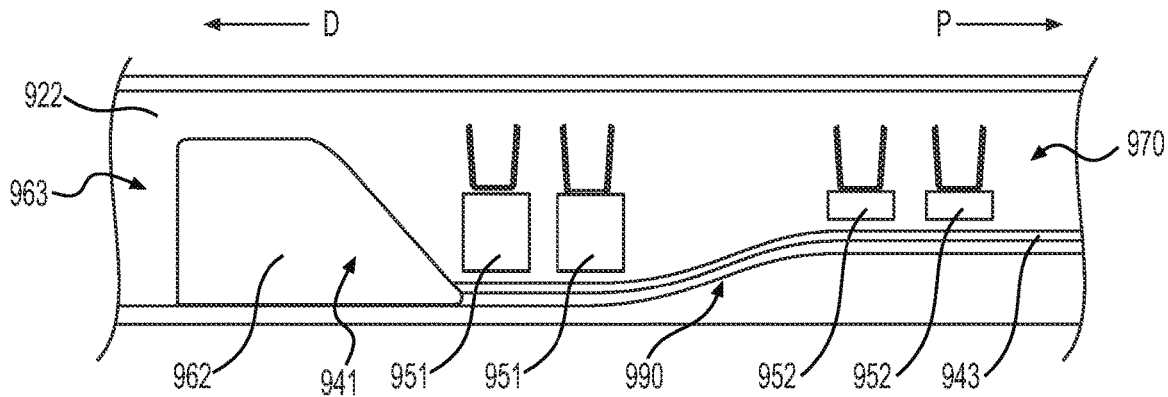
FIG. 9 is a side view of a portion of an exemplary medical device, according to aspects of this disclosure.

FIG. 9 shows a side view of cartridge 922 with a portion of cartridge 922 removed to show stapling portion 963 of channel 970. Cartridge 922 may include ramp portion 990 and may have any of the features described hereinabove in relation to cartridge 622. Actuation sled 941 is shown entirely within cartridge 922 in an undeployed state, which may provide an atraumatic tip of a stapler device and may avoid unwanted cutting of tissue during movement of the stapler device through a patient's body because knife portion (not shown) of actuation sled 941 is also not exposed (like in FIG. 7 described above). Actuation wire 943 may be pulled proximally to move actuation sled 941 across ramp portion 990. Ramp portion 962 of actuation sled 941 is shown positioned within actuation portion 963 of channel 970. Pistons or spacers 951, 952 may have any of the attributes previously described in relation to pistons/spacers 351 in FIG. 3. Spacers 951 that are distal to ramp 990 may be taller relative to spacers 952 that are proximal to ramp 990, to allow actuation sled 941 to deploy fasteners when positioned proximal to ramp portion 990 of channel 970. This allows ramp portion 962 of actuation sled 941 to deploy fasteners while knife portion (not shown) is undeployed (or fully within cartridge 922). Spacers 951 may be distal to spacers 952, and the height of spacers 951 may be larger than the height of spacers 952. In some examples (not shown), a cartridge may include spacers with a plurality of different heights to deploy staples as actuation sled 941 moves across a ramp portion 990 of cartridge 922. In order to deploy staples using actuation sled 941 and allow a "staple line" to start ahead of (distal to) the "cut line," at least one fastener is deployed prior to deployment of the knife portion (not shown) of actuation sled 941.

FIG. 10 shows another example of an actuation sled 1041 that may be incorporated into a stapler device. Actuation sled 1041 may include a ramp portion 1062, a knife portion 1060, a connecting portion 1064, and an actuation wire 1043. Actuation sled 1041 may have any of the features described herein in relation to other actuation sleds 241, 341, 541, 941. As shown in FIG. 10, knife portion 1060 may be longitudinally offset from ramp portion 1062 by distance A, such that ramp portion 1062 is proximal to knife portion 1060. Distance A represents a distance between a distalmost surface of knife portion 1060 and a distalmost surface of ramp portion 1062. In an example, all of knife portion 1060 is distal of all of ramp portion 1062. By providing an actuation sled 1041 with knife portion 1060 longitudinally offset from ramp portion 1062, fasteners may be deployed from a cartridge prior to deployment of knife portion 1060. Also, by providing an actuation sled 1041 with knife portion 1060 longitudinally offset from ramp portion 1062, the stapler device may fasten tissue together prior to cutting tissue proximate to the staple line.

FIGS. 11A, 11B, 12A, and 12B show an alternative embodiment of an actuation sled 1141 that may be incorporated into a stapler device. Actuation sled 1141 may include a ramp portion 1162, a knife portion 1160, a connecting portion 1164, and an actuation wire 1143. Actuation sled 1141 may have any of the features described herein in relation to other actuation sleds 241, 341, 541, 941, 1041. Knife portion 1160 may be flexible (including flexible towards and away from tissue spaced between the cartridge and the anvil). Knife portion 1160 may be biased towards a position in which blade portion 1160 extends upward in a direction transverse to a central longitudinal axis C of actuation sled 1141 and approximately parallel to ramp portion 1162. Knife portion 1160 may be rotatable/pivotable relative to connecting portion 1164, may be configured to be rotated into a relatively flattened state (shown in FIGS. 11A and 12A), and may be configured to transition to an extended position (shown in FIGS. 11B and 12B) when released.

FIG. 11A shows an outline of a portion of a cartridge 1180 (dashed lines) which holds knife portion 1160 in a suppressed (rotated) position. FIG. 12A shows a cross-sectional view of a portion of cartridge 1180 including a cavity shown by the outline of a portion of cartridge 1180 in FIG. 11A. Knife portion 1160 is shown in a suppressed position in FIG. 12A in which cartridge 1180 prevents knife portion 1160 from moving upward towards a top surface 1292 of cartridge 1180. A chamber 1270 of cartridge 1180 may be configured to receive knife portion 1160 when knife portion 1160 is in a suppressed position, and chamber 1270 may be configured to hold knife portion 1160 in a suppressed position preventing knife portion 1160 from extending outward from cartridge 1180. While knife portion 1160 is suppressed by chamber 1270, ramp portion 1162 may deploy fasteners as actuation sled 1141 moves through chamber 1270, allowing actuation sled 1141 to deploy fasteners without knife portion 1160 deployed outside of cartridge 1180.

FIGS. 11B and 12B show actuation sled 1141 in a deployed position with knife portion 1160 extending upward and parallel to ramp portion 1162. In a deployed position, knife portion 1160 may be configured to extend through an elongate channel 1261 of cartridge 1180, which may be similar to elongate channel 424 of cartridge 422. Since knife portion 1160 may be biased towards a deployed position, when a user moves actuation sled 1141 proximally to transition actuation sled from a position shown in FIG. 12A to a position shown in FIG. 12B, knife portion 1160 may move into elongate channel 1261. The distalmost end of elongate channel 1261 may be proximal to the distalmost end of chamber 1270. As shown in FIG. 12B, when knife portion 1160 transitions to a deployed state, a portion of knife portion 1160 may be exposed outside of cartridge 1180 to cut tissue. Elongate channel 1261 may be configured to align with knife portion 1160 such that knife portion 1160 moves into elongate channel 1261 once actuation sled 1141 is positioned at a portion of chamber 1270 in which chamber 1270 and elongate channel 1261 are connected.

In operation, actuation sled 1141 may be initially positioned at a distal end of cartridge 1180 and within chamber 1270 such that knife portion 1160 is in an undeployed state and knife portion 1160 does not extend radially outward from central longitudinal axis C of actuation sled 1141 farther than ramp portion 1162, as shown in FIG. 12A. The user may pull actuation wire 1143 proximally to move actuation sled 1141 proximally such that actuation sled 1141 moves to a portion of chamber 1270 connected to elongate channel 1261. Once the user pulls actuation sled 1141 to a position in which elongate channel 1261 is adjacent to knife portion 1160, actuation sled 1141 may transition to a deployed state and knife portion 1160 may move within elongate channel 1261. A portion of knife portion 1160 may move exterior to cartridge 1180 in order to engage tissue, as shown in FIG. 12B. When transitioning from an undeployed state to a deployed state, knife portion 1160 may rotate along a longitudinal axis of knife portion 1160. Note actuation sled 1141 may be incorporated into any of the stapler cartridges discussed herein.

FIGS. 13-17 show various mechanisms for coupling an actuation sled (such as actuation sled 1360) and a knife (such as knife 1362) to a single actuation wire (such as actuation wire 1343) to allow actuation and deployment of fasteners from a staple cartridge and deployment of a knife to cut tissue. Any of the components shown in FIGS. 13-17 may be incorporated into any of the cartridges discussed herein for use in a stapler device.

Figure 13:
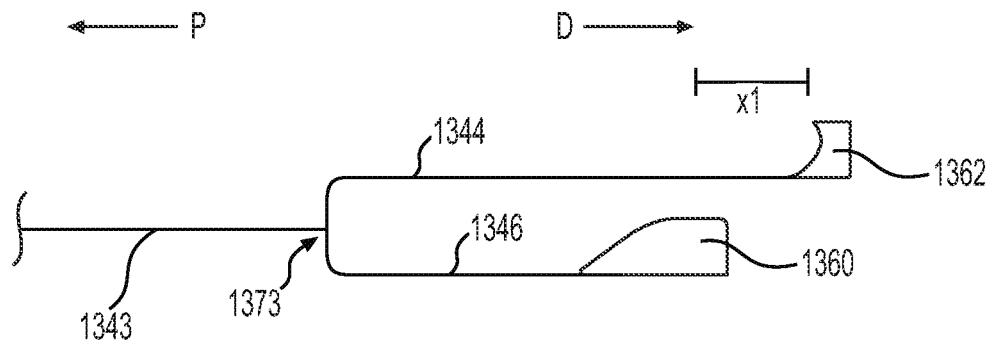
FIG. 13 is a perspective view of a portion of an exemplary actuation assembly, according to aspects of the present disclosure.

FIG. 13 shows a knife 1362 and an actuation sled 1360 coupled to an actuation wire 1343 via a first connecting wire 1344 and a second connecting wire 1346. First connecting wire 1344 is coupled to knife 1362 at the distalmost end of connecting wire 1344 and is coupled to actuation wire 1343 at its proximalmost end (shown at junction 1373). Second connecting wire 1346 is coupled to actuation sled 1360 at its distalmost end and is coupled to actuation wire 1343 at its proximalmost end (also shown at junction 1373). The length of first connecting wire 1344 is greater than the length of second connecting wire 1346, which creates a distance X1 that knife 1362 is offset from actuation sled 1360. Distance X1 may be a large enough distance to allow actuation sled 1360 to fully deploy at least one fastener before knife 1362 engages tissue. For example, as the user pulls actuation wire 1343 proximally, actuation sled 1360 may deploy at least one fastener from the cartridge before knife 1362 engages tissue. In some examples, distance X1 may be approximately 1-10 mm. Distance X1 that knife 1362 is offset from actuation sled 1360 may control the amount of delay between the actuation sled 1360 deployment of fasteners and the deployment of knife 1362 to engage tissue. In some examples, distance X1 may be approximately 1-2 mm, or any other suitable distance. Knife 1362 may be covered by a cap in the stapler device, or a portion of the cartridge, prior to deployment to prevent unwanted engagement of knife 1362 with tissue during movement of a stapler device through a patient's body. When actuation wire 1343 is pulled proximally, actuation sled 1360 will move proximally within a cartridge of a stapler device ahead of knife 1362. While connecting wire 1344 is shown coupled to actuation wire 1343 at a position proximal to actuation sled 1360, in other embodiments connecting wire 1344 may be coupled to actuation sled 1360 forming a chain in which actuation wire 1343 pulls actuation sled 1360, and actuation sled 1360 pulls connecting wire 1344 to pull knife 1362. Actuation sled 1360 and knife 1362 may be configured to move within two separate channels of a cartridge in a stapler device.

Figure 14:
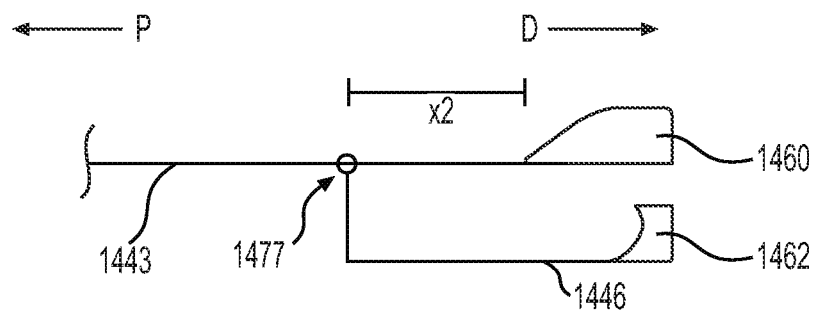
FIG. 14 is a perspective view of a portion of an exemplary actuation assembly, according to aspects of the present disclosure.

FIG. 14 shows an alternative embodiment of actuation sled 1460, a knife 1462, and an actuation wire 1443. Actuation wire 1443 may be directly coupled to actuation sled 1460, and knife 1462 may be coupled to a connecting wire 1446 which is moveably coupled to actuation wire 1443. In some examples, connecting wire 1446 may be moveably coupled to actuation wire 1443 via a ring coupler 1477. Ring coupler 1477 may be a circular wire that extends around actuation wire 1443 and is configured to slide along actuation wire 1443. Ring coupler 1477 may form a circular ring of wire or other material, and may be sized to allow movement of actuation wire 1443 through the circular ring.

Initially, actuation sled 1460 and knife 1462 may be positioned within a cartridge of a stapling device at approximately the same position along a longitudinal axis of a cartridge (though separated along a width dimension). A user may pull actuation wire 1443 proximally to move actuation sled 1460 to deploy fasteners. When a user initially pulls actuation wire 1443 proximally, ring coupler 1477 may slide along actuation wire 1443 and knife 1462 may not move. Once actuation wire 1443 is moved proximally a distance X2, ring coupler 1477 may be adjacent to actuation sled 1460 and actuation sled 1460 may prevent ring coupler 1477 from further moving/sliding relative to actuation wire 1443 and actuation sled 1460. Once ring coupler 1477 is adjacent to and/or in contact with actuation sled 1460, knife 1462 and connecting wire 1446 may be pulled via the proximal movement of actuation wire 1443 to deploy knife 1462.

Figure 15:
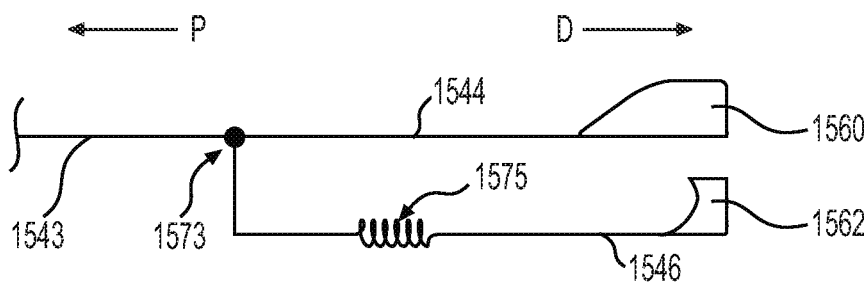
FIG. 15 is a perspective view of a portion of an exemplary actuation assembly, according to aspects of the present disclosure.

FIG. 15 shows another embodiment of actuation sled 1560, a knife 1562, and an actuation wire 1543. Actuation sled 1560, knife 1562, and actuation wire 1543 may have any of the features described herein in relation to actuation sled 1360, 1460, knife 1362, 1462, and actuation wire 1343, 1443. Actuation sled 1560 is fixedly coupled to connecting wire 1544 which is fixedly coupled to actuation wire 1543 at junction 1573. Knife 1562 is fixedly coupled to connecting wire 1546, and connecting wire 1546 is fixedly coupled to actuation wire 1543 at junction 1573. Connecting wire 1546 includes a spring portion 1575, and spring portion 1575 may be configured to expand before providing the adequate amount of force to pull knife 1562. Spring portion 1575 may be biased towards a contracted position. Spring portion 1575 may be configured to expand a first distance which may be the distance actuation sled 1560 is offset from knife 1562. When a user pulls actuation wire 1543 proximally, actuation sled 1560 may move proximally and spring portion 1575 may expand, while knife 1562 may remain stationary due to the friction force between knife 1562 and the cartridge knife 1562 is positioned within. When spring portion 1575 is expanded to its maximum expanded state, spring portion 1575 may then provide enough force to pull knife 1562 and overcome the friction force between knife 1562 and the cartridge knife 1562 is positioned within. Once spring portion 1575 is expanded to a state that provides enough force to pull knife 1562, knife 1562 and actuation sled 1560 may be pulled simultaneously by the user pulling actuation wire 1543 proximally.

Figure 16:
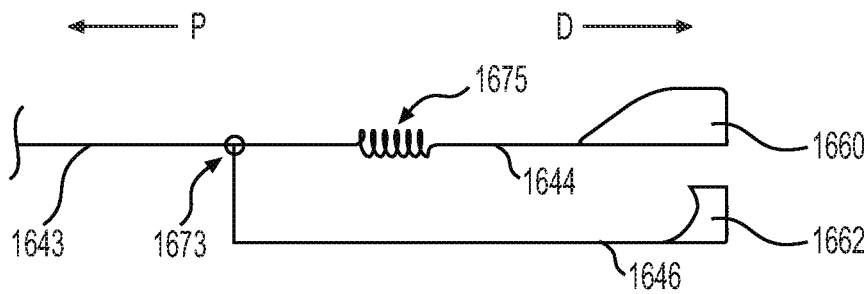
FIG. 16 is a perspective view of a portion of an exemplary actuation assembly, according to aspects of the present disclosure.

FIG. 16 shows another embodiment of actuation sled 1660, a knife 1662, and an actuation wire 1643. Actuation sled 1660, knife 1662, and actuation wire 1643 may have any of the features described herein in relation to actuation sled 1360, 1460, 1560, knife 1362, 1462, 1562 and actuation wire 1343, 1443, 1543. Knife 1662 may be coupled to actuation wire 1643 via connecting wire 1646. Connecting wire 1646 may be moveably coupled to actuation wire 1643 via a ring coupler 1673, and ring coupler 1673 may have any of the features of ring coupler 1477 described hereinabove. Actuation sled 1660 may be fixedly coupled to connecting wire 1644, and connecting wire 1644 may include a spring portion 1675. Spring portion 1675 may have any of the features described hereinabove in relation to spring portion 1575, and spring portion 1675 may be fixedly coupled to actuation wire 1643. When actuation wire 1643 is pulled proximally, ring coupler 1673 may travel along actuation wire 1643 until ring coupler 1673 contacts a proximal end of spring portion 1675. Once ring coupler 1673 contacts spring portion 1675, spring portion 1675 may compress until spring portion 1675 can provide enough force to pull actuation sled 1660 and knife 1662 proximally. In some examples, spring portion 1675 must be fully collapsed to provide enough force to pull actuation sled 1660 and knife 1662 proximally when a user pulls actuation wire 1643 proximally.

In operation, a user pulls actuation wire 1643 proximally which will first expand spring portion 1675 until spring portion 1675 provides enough force to pull actuation sled 1660. The actuation sled 1660 may move proximally as the user continues to pull actuation wire 1643 proximally, and ring coupler 1673 may move along actuation wire 1643 until ring coupler 1673 contacts spring portion 1675. Once ring coupler 1673 contacts spring portion 1675, spring portion 1675 may further compress due to the additional force applied by knife 1662 and connecting wire 1646 due to a friction force between knife 1662 and the cartridge that knife 1662 is positioned within. Once spring portion 1675 has been compressed to a position that may provide enough force to pull both actuation sled 1660 and knife 1662 (and overcome the friction force between the actuation sled 1660 and the cartridge, and the friction force between the knife 1662 and the cartridge), both actuation sled 1660 and knife 1662 may move proximally through the cartridge.

Figure 17:
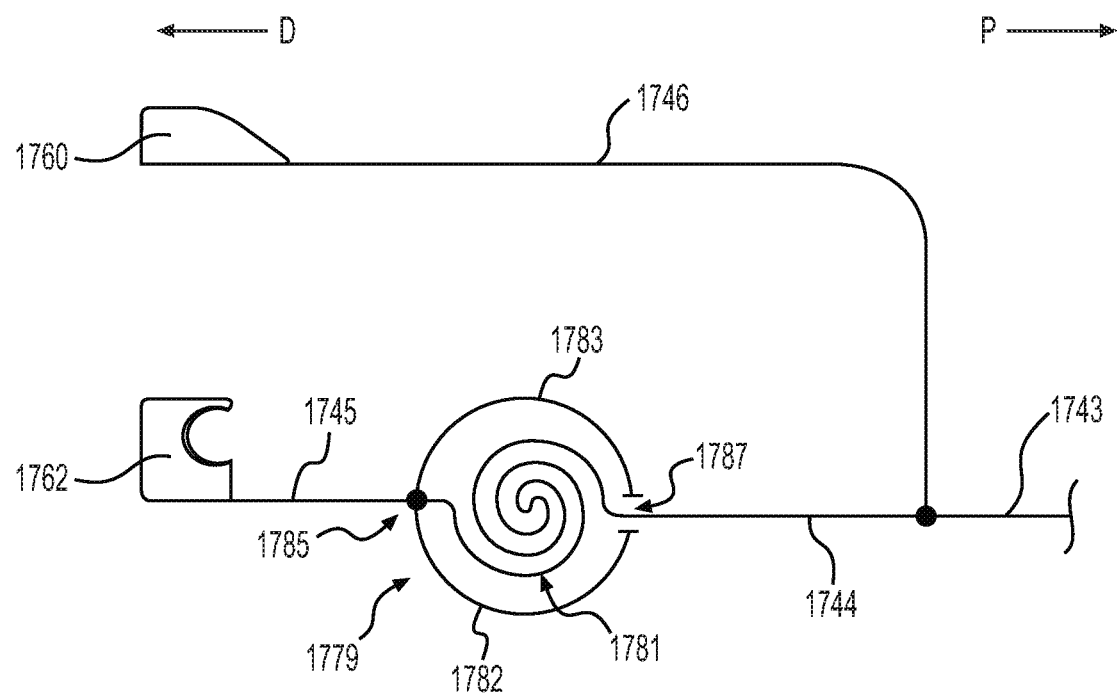
FIG. 17 is a perspective view of a portion of an exemplary actuation assembly, according to aspects of the present disclosure.

FIG. 17 shows an alternative embodiment of actuation sled 1760, a knife 1762, and an actuation wire 1743. Actuation sled 1760, knife 1762, and actuation wire 1743 may have any of the features described herein in relation to actuation sled 1360, 1460, 1560, 1660, knife 1362, 1462, 1562, 1662, and actuation wire 1343, 1443, 1543, 1643. Actuation sled 1760 may be fixedly coupled to actuation wire 1743 via connecting wire 1746. Knife 1762 may be coupled via connecting wire 1745 to a spring-loaded coil 1781 contained within a housing 1782, 1783. Spring-loaded coil 1781 may be contained within housing 1782, 1783 and may be coupled to connecting wire 1744. Connecting wire 1744 may be fixedly coupled to actuation wire 1743. Spring-loaded coil 1781 may be configured to unravel a set distance when pulled proximally via actuation wire 1743, and once the set distance is unraveled from spring-loaded coil 1781, spring-loaded coil 1781 may provide enough force to pull knife 1762 proximally. When a force is not acting on spring-loaded coil 1781, spring loaded coil 1781 may be configured to wrap itself within housing 1782, 1783 (e.g. spring loaded coil 1781 is biased towards a wrapped positioned within housing 1782, 1783). By wrapping itself when not under tension, spring-loaded coil 1781 may avoid any excess length of spring-loaded coil 1781 and/or connecting wire 1744 that may be loose within a cartridge or other portion of a stapler device from becoming excessively tortuous and/or potentially tangling/locking a portion of the device. Spring loaded coil 1781 may be biased towards a position within housing 1782, 1783.

In operation, knife 1762 may be held at its initial position via friction from its interference with the cartridge (not shown) knife 1762 is positioned within. A user may pull actuation wire 1743 proximally, which may pull actuation sled 1760 proximally. As actuation sled 1760 moves proximally, actuation sled 1760 may deploy fasteners from the cartridge. While actuation sled 1760 moves proximally and deploys at least one fastener from cartridge, the spring-loaded coil 1781 may unravel until the spring-loaded coil has reached its unraveling limit (or maximum distance spring-loaded coil may unravel before pulling knife 1762 proximally). Once spring-loaded coil 1781 has reached its unraveling limit, both actuation sled 1760 and knife 1762 may be translated proximally via the user pulling actuation wire 1743. Proximal movement of knife 1762 may be delayed by the distance that spring-loaded coil 1781 unraveled.

Each of the actuation sled and knife actuation assemblies shown in FIGS. 13-17 may be incorporated into any of the stapler devices described herein, and may provide a means to actuate both a fastener deployment mechanism and a tissue resection mechanism using a single actuation wire.

Each of the aforementioned apparatuses and devices may be used to couple and/or cut tissue. In some examples, a user may introduce an endoscope into a patient's body and move the endoscope towards a target area. The user may locate a target area (such as a tumor or other diseased tissue) present in a body lumen of a subject using the endoscope by directly visualizing the target area using an image sensor (such as a camera). Once the user has positioned the endoscope's distal end proximate to a target area, the user may position a tissue acquisition tool within a working channel of the endoscope, if such a tool is not already present. When the distal end of the endoscope is positioned at the target area, the user may actuate the stapler device to an open position creating a space between the stapler's anvil and body. The user may then introduce the tissue acquisition tool to the target area and position the tissue acquisition tool between or close to the active portion of the stapler device, e.g. the space between the stapler device's anvil and body. The user may then grasp tissue with the tissue acquisition tool and move tissue into the stapler device's active portion. Once tissue is positioned within the stapler device's active portion, the user may move the stapler device's anvil and body to a closed position and clamp down on the grasped tissue with the stapler device. The user may then actuate an actuator in order to pull on an actuation wire, thus moving an actuation sled of the stapler device proximally. By moving the actuation sled proximally via an actuator, the user may deploy fasteners into the clamped tissue and against the stapler device's anvil. In some examples, the user may simultaneously actuate, via the same actuation wire, a knife in the stapler device to cut portions of the target tissue after fastening tissue together via fasteners.

By providing means to fasten tissue together using a stapler device before applying a tissue resection device (such as cutting tissue with a knife), the user may avoid unwanted leakage of bodily fluid caused when resecting tissue or removing a polyp from a patient's body. For example, a user may first staple tissue surrounding a polyp to form a seal of healthy tissue around the polyp, and then cut the tissue adjacent to the seal.

By providing a stapler instrument that may actuate multiple features of the stapler instrument, such as stapling tissue and cutting tissue features, simultaneously using a single actuation wire, the size of the stapler instrument may be reduced and may facilitate operating the stapler instrument in conjunction with an endoscope or other medical device.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A tissue fastening device comprising:
a body configured to include a plurality of fasteners;
an anvil rotatable relative to the body;
a tissue cutting device, wherein the body comprises a longitudinal channel configured to receive the tissue cutting device;
a fastener actuator configured to move proximally relative to the body to deploy the plurality of fasteners from the body;
a first spacer and a second spacer, wherein each of the first spacer and the second spacer is within the body and configured to deploy a fastener; and
an actuation wire coupled to the tissue cutting device and the fastener actuator;
wherein actuation of the actuation wire causes the fastener actuator to deploy at least one of the plurality of fasteners into tissue distally of where tissue is to be cut by the tissue cutting device, wherein the tissue cutting device and the fastener actuator are monolithic, and wherein the tissue cutting device is immovable in all directions relative to the fastener actuator;
wherein the body includes a first wall and a second wall, opposite the first wall, wherein the first wall is closer than the second wall to the anvil, and wherein the second wall includes a ramp portion thereon that is configured to transition the tissue cutting device between 1) an undeployed state in which the tissue cutting device is within the body and incapable of cutting tissue, and 2) a deployed state in which the tissue cutting device is exposed outside of the body and capable of cutting tissue; and
wherein the first spacer is disposed distally of the ramp portion, and the second spacer is disposed proximally of the ramp portion, and wherein the first spacer has a larger height than the second spacer.

2. The device of claim 1, wherein the tissue cutting device and the fastener actuator are elements of a U-shaped component; wherein a first leg of the U-shaped component includes the tissue cutting device, wherein a second leg of the U-shaped component includes the fastener actuator, and wherein the first leg and the second leg are substantially parallel.

3. The device of claim 1, wherein the tissue cutting device is distal to the fastener actuator.

4. The device of claim 1, wherein activation of the actuation wire causes the fastener actuator to deploy the at least one of the plurality of fasteners before causing the tissue cutting device to cut tissue.

5. The device of claim 1, wherein the tissue cutting device and the fastener actuator are configured to move proximally across the ramp portion in order to transition the tissue cutting device.

6. The device of claim 1, wherein actuation of the actuation wire causes the fastener actuator to deploy at least one of the plurality of fasteners into tissue approximately 8 mm distally of where tissue is to be cut.

7. A tissue fastening device comprising:
a body configured to include a plurality of fasteners, wherein the body includes a ramp portion;
an anvil rotatable relative to the body;
a tissue cutting device, wherein the body comprises a longitudinal channel configured to receive the tissue cutting device;
a fastener actuator configured to move proximally relative to the body to deploy the plurality of fasteners from the body, wherein the tissue cutting device is immovable in all directions relative to the fastener actuator;
a first spacer and a second spacer, wherein each of the first spacer and the second spacer is within the body and configured to deploy a fastener, wherein the first spacer is disposed distally of the ramp portion, wherein the second spacer is disposed proximally of the ramp portion, and wherein the first spacer has a larger height than the second spacer; and
an actuation wire coupled to the tissue cutting device and the fastener actuator, wherein actuation of the actuation wire causes the fastener actuator to deploy at least one of the plurality of fasteners into tissue prior to the tissue cutting device and the fastener actuator contacting the ramp portion, thereby causing the tissue cutting device to cut tissue.

8. The device of claim 7, wherein the longitudinal channel is configured so that it receives the tissue cutting device in a position to cut tissue, proximally of an entirety of a distalmost fastener of the plurality of fasteners.

9. The device of claim 8, wherein the plurality of fasteners define a line of fasteners, and a distalmost part of the line is distal to a distalmost end of a cut line defined by the longitudinal channel.

10. The device of claim 8, wherein a distalmost end of the longitudinal channel is approximately 8 mm proximal of the distalmost fastener.

11. The device of claim 7, wherein the tissue cutting device is distal to the fastener actuator.

12. A tissue fastening device comprising:
a body configured to include a plurality of fasteners;
an anvil rotatable relative to the body;
a tissue cutting device, wherein the body comprises a longitudinal channel configured to receive the tissue cutting device;
a fastener actuator configured to move proximally relative to the body to deploy the plurality of fasteners from the body, wherein the tissue cutting device is immovable in all directions relative to the fastener actuator; and
an actuation wire coupled to the tissue cutting device and the fastener actuator, wherein actuation of the actuation wire causes the fastener actuator to deploy at least three fasteners into tissue distally of a distalmost location where tissue is to be cut by the tissue cutting device;
wherein the body includes a first wall and a second wall, opposite the first wall, wherein the first wall is closer than the second wall to the anvil, wherein the second wall includes a ramp portion thereon that is configured to transition the tissue cutting device between 1) an undeployed state in which the tissue cutting device is within the body and incapable of cutting tissue, to 2) a deployed state in which the tissue cutting device is exposed outside of the body and capable of cutting tissue, wherein the device further comprising a first spacer and a second spacer, wherein each of the first spacer and the second spacer is within the body and configured to deploy a fastener, wherein the first spacer is disposed distally of the ramp portion, wherein the second spacer is disposed proximally of the ramp portion, and wherein the first spacer has a larger height than the second spacer.

13. The device of claim 12, wherein entireties of the at least three fasteners are deployed into tissue distally of where tissue is to be cut.

14. The device of claim 12, wherein the fastener includes a middle section and two arms, each arm having a free end pointing away from the middle section, and wherein the free ends of the two arms point away from the ramp portion.

15. The device of claim 12, wherein the tissue cutting device and the fastener actuator are elements of a U-shaped component; wherein a first leg of the U-shaped component includes the tissue cutting device, wherein a second leg of the U-shaped component includes the fastener actuator, and wherein the first leg and the second leg are substantially parallel and comprise the tissue cutting device and the fastener actuator.

16. The device of claim 12, wherein the tissue cutting device is distal to the fastener actuator in all configurations of the device.

\* \* \* \* \*